(12) United States Patent
Quintanar et al.

(10) Patent No.: US 10,442,275 B2
(45) Date of Patent: Oct. 15, 2019

(54) VENT REGISTER WITH HOLLOW ACTUATOR CARRYING A FRAGRANCE ELEMENT

(71) Applicant: FORD GLOBAL TECHNOLOGIES, LLC, Dearborn, MI (US)

(72) Inventors: Raul Ahuitzol Quintanar, San Juan del Rio (MX); Francisco Javier Villanueva, Los Pastores (MX)

(73) Assignee: Ford Global Technologies, LLC, Dearborn, MI (US)

( * ) Notice: Subject to any disclaimer, the term of this patent is extended or adjusted under 35 U.S.C. 154(b) by 306 days.

(21) Appl. No.: 15/204,727

(22) Filed: Jul. 7, 2016

(65) Prior Publication Data

US 2018/0009293 A1    Jan. 11, 2018

(51) Int. Cl.
*B60H 3/00* (2006.01)
*A61L 9/12* (2006.01)
*B60H 1/34* (2006.01)
*B60H 1/00* (2006.01)

(52) U.S. Cl.
CPC ............ *B60H 3/0028* (2013.01); *A61L 9/122* (2013.01); *B60H 1/0065* (2013.01); *B60H 1/3421* (2013.01); *B60H 3/00* (2013.01); *A61L 2209/15* (2013.01); *A61L 2209/16* (2013.01); *B60H 2001/3471* (2013.01)

(58) Field of Classification Search
CPC ...... B60H 1/3428; B60H 3/0028; B60H 3/00; B60H 2001/3471; B60H 1/0065; A61L 2209/15; A61L 2209/16
See application file for complete search history.

(56) References Cited

U.S. PATENT DOCUMENTS

| | | | | |
|---|---|---|---|---|
| 4,813,344 A * | 3/1989 | Greif | ............ | A61L 9/12 239/58 |
| 5,422,078 A * | 6/1995 | Colon | ............ | A61L 9/12 239/54 |
| 5,478,505 A * | 12/1995 | McElfresh | ............ | A61L 9/122 239/57 |
| 6,123,906 A * | 9/2000 | Farmer | ............ | A61L 9/12 239/36 |
| 6,264,887 B1 | 7/2001 | Farmer | | |
| 8,460,609 B1 * | 6/2013 | Wheatley | ............ | A61L 9/042 422/120 |
| 8,765,063 B1 * | 7/2014 | Mazzilli | ............ | A61L 9/12 239/53 |

(Continued)

FOREIGN PATENT DOCUMENTS

| | | | | |
|---|---|---|---|---|
| CH | 705826 A2 * | 5/2013 | ............ | A61L 9/122 |
| DE | 102008021460 A1 | 11/2009 | | |

(Continued)

OTHER PUBLICATIONS

English Machine Translation of DE1004489484.
English Machine Translation of DE102008021460A1.

*Primary Examiner* — Steven S Anderson, II
(74) *Attorney, Agent, or Firm* — Vichit Chea; King & Schickli, PLLC

(57) ABSTRACT

A vent register includes an adjustable vane, an actuator carried on the adjustable vane and a fragrance element carried on the actuator. A related method of distributing a fragrance in a passenger compartment of a motor vehicle is also disclosed.

3 Claims, 3 Drawing Sheets

(56) References Cited

U.S. PATENT DOCUMENTS

| | | | |
|---|---|---|---|
| 8,834,240 B2 * | 9/2014 | Azzouz | B60H 1/3435 |
| | | | 454/143 |
| 2004/0072532 A1 | 4/2004 | Cho | |
| 2004/0223891 A1 * | 11/2004 | Brown | A61L 9/125 |
| | | | 422/124 |
| 2011/0207393 A1 * | 8/2011 | Kober | B60H 1/3421 |
| | | | 454/324 |
| 2014/0217623 A1 | 8/2014 | Franks | |

FOREIGN PATENT DOCUMENTS

| | | | | |
|---|---|---|---|---|
| DE | 10044894 B4 | 2/2016 | | |
| FR | 2893539 A1 * | 5/2007 | ........... | B60H 1/3442 |
| FR | 3028926 A1 * | 5/2016 | ........... | B60H 1/3421 |
| GB | 2196421 A * | 4/1988 | ........... | B60H 1/3421 |
| KR | 20090126784 A | 12/2009 | | |
| KR | 101201666 B1 | 11/2012 | | |

* cited by examiner

VENT REGISTER WITH HOLLOW ACTUATOR CARRYING A FRAGRANCE ELEMENT

TECHNICAL FIELD

This document relates generally to the heating, ventilating and air conditioning field and, more particularly, to a vent register incorporating a hollow actuator that holds a fragrance element whereby a portion of the air travelling through the vent register flows through the actuator and across the fragrance element so as to freshen the air.

BACKGROUND

The concept of providing a vent register with one or more adjustable vanes for directing air from a ventilation duct into a conditioned air space is well known in the art. One or more such vent registers are commonly provided on motor vehicles.

Many drivers utilize different types of scent or fragrance elements in order to improve or freshen the quality of the air in the passenger compartment of a motor vehicle. Toward this end, many drivers purchase fragrance-containing devices that are hung on the vent register so as to be in the flow of air being expelled from the vent register into the passenger compartment or conditioned space of the motor vehicle. As should be appreciated, such devices are often unsightly. Further, they tend to restrict airflow from the vent registers thereby reducing the performance of the heating, ventilation and air conditioning (HVAC) system of the motor vehicle.

This document relates to a novel vent register of improved design incorporating an adjustable vane for directing airflow from the vent register. An actuator carried on that adjustable vane and within the flow of the air coming from the vent register is hollow and incorporates a fragrance element for freshening the air being distributed by the HVAC system into the passenger compartment of the motor vehicle. In this way it is possible to add a pleasing scent to the air being delivered to the passenger compartment through the vent register while maintaining an overall aesthetically pleasing appearance. Further, the fragrance element held in the actuator may be easily changed as desired in order to renew the current scent or change to a different scent.

SUMMARY

In accordance with the purposes and benefits described herein, a vent register is provided. That vent register comprises an adjustable vane, an actuator carried on the adjustable vane and a fragrance element carried on the actuator.

The actuator may include a first section, a second section and a scent compartment defined between the first section and the second section. The first section may include a receiver for holding the fragrance element. The second section may be fixed to the adjustable vane.

The second section may include an air inlet in communication with the scent compartment. Further, the second section may include an air outlet in communication with the scent compartment.

The vent register may further include a resilient latch for securing the first section with the second section and thereby capturing the fragrance element in the scent compartment where it is held in the stream of air being distributed through the vent register.

The fragrance element may comprise a fragrance strip and the receiver may include a lug that engages the fragrance strip. As should be appreciated, the fragrance strip may be replaceable. This allows one to renew the current fragrance or select a new and different fragrance as desired.

In one possible embodiment the second section of the actuator is integral with the adjustable vane so as to be a single component structure.

In accordance with yet another aspect, a method is provided of distributing a fragrance in a passenger compartment of a motor vehicle. That method comprises the step of directing airflow from a ventilation duct through a scent compartment in an adjustment vane actuator of the vent register. Still further the method may include the step of positioning a fragrance element in the scent compartment.

In the following description, there are shown and described several preferred embodiments of the vent register. As it should be realized, the vent register is capable of other, different embodiments and its several details are capable of modification in various, obvious aspects all without departing from the vent register as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the vent register and together with the description serve to explain certain principles thereof. In the drawing figures.

Reference will now be made in detail to the present preferred embodiments of the vent register, examples of which are illustrated in the accompanying drawing figures.

DETAILED DESCRIPTION

Figure 1:
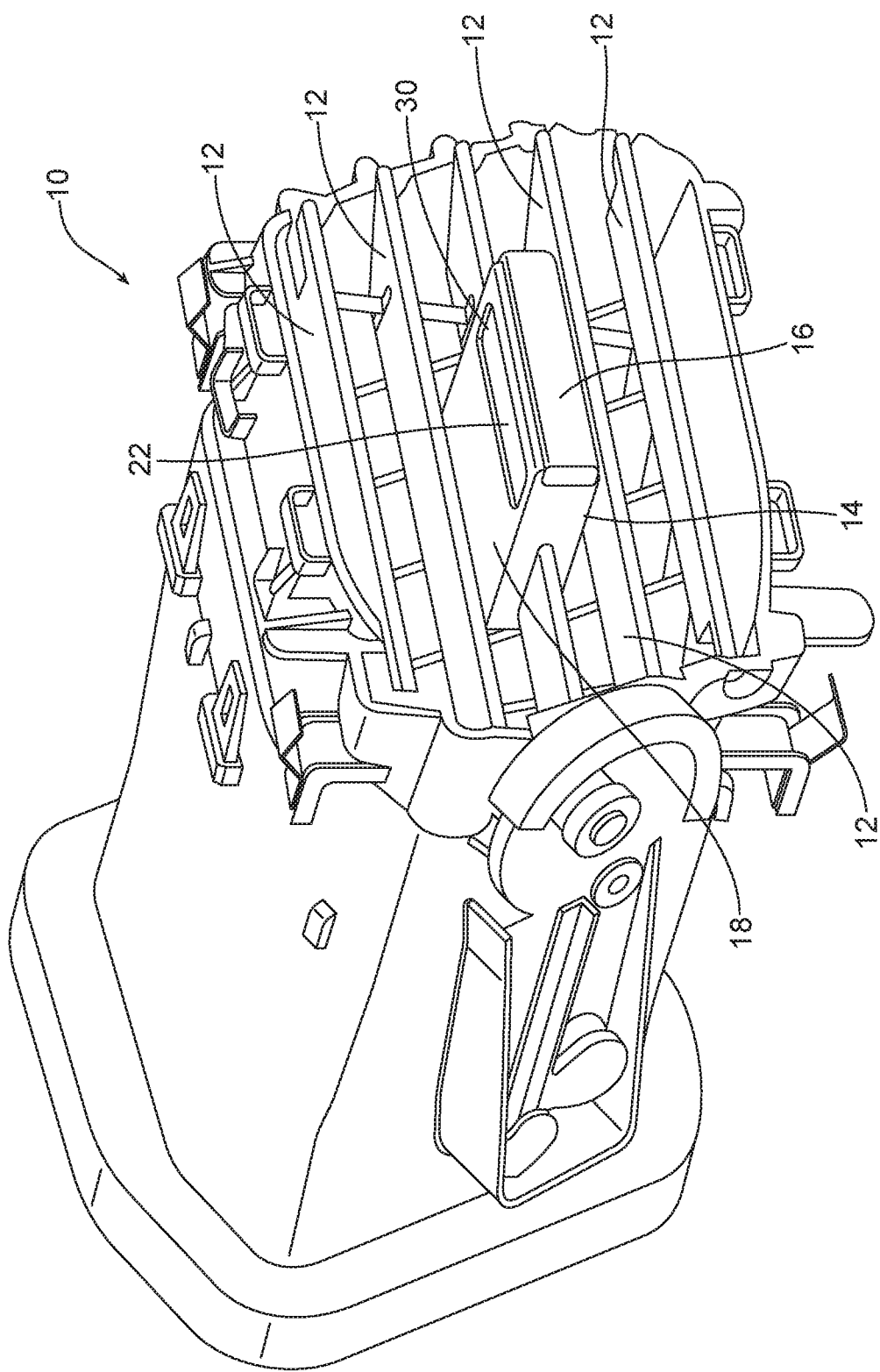
FIG. 1 is a detailed perspective view of a vent register incorporating an adjustable vane, an actuator carried on that adjustable vane by which the position or spatial orientation of the adjustable vane is adjusted, and a fragrance element carried on the actuator.

Reference is now made to FIG. 1 illustrating a vent register 10 of the type that is positioned in communication with the delivery end of a ventilation duct and functions to deliver an airstream from that ventilation duct to a conditioned space such as a passenger compartment of a motor vehicle. In the illustrated embodiment, the vent register 10 includes a plurality of adjustable vanes 12 that may be angularly oriented to direct an airstream from the ventilation duct in a desired direction into the conditioned space. An actuator 14 carried on one of the adjustable vanes 12 allows one to adjust the angular orientation of all of the adjustable vanes 12 by means of a linkage or other mechanism of a type known in the art. The details of such a mechanism or linkage are not discussed in this document as they are not relevant to the novel aspects of the vent register 10.

Figure 2:
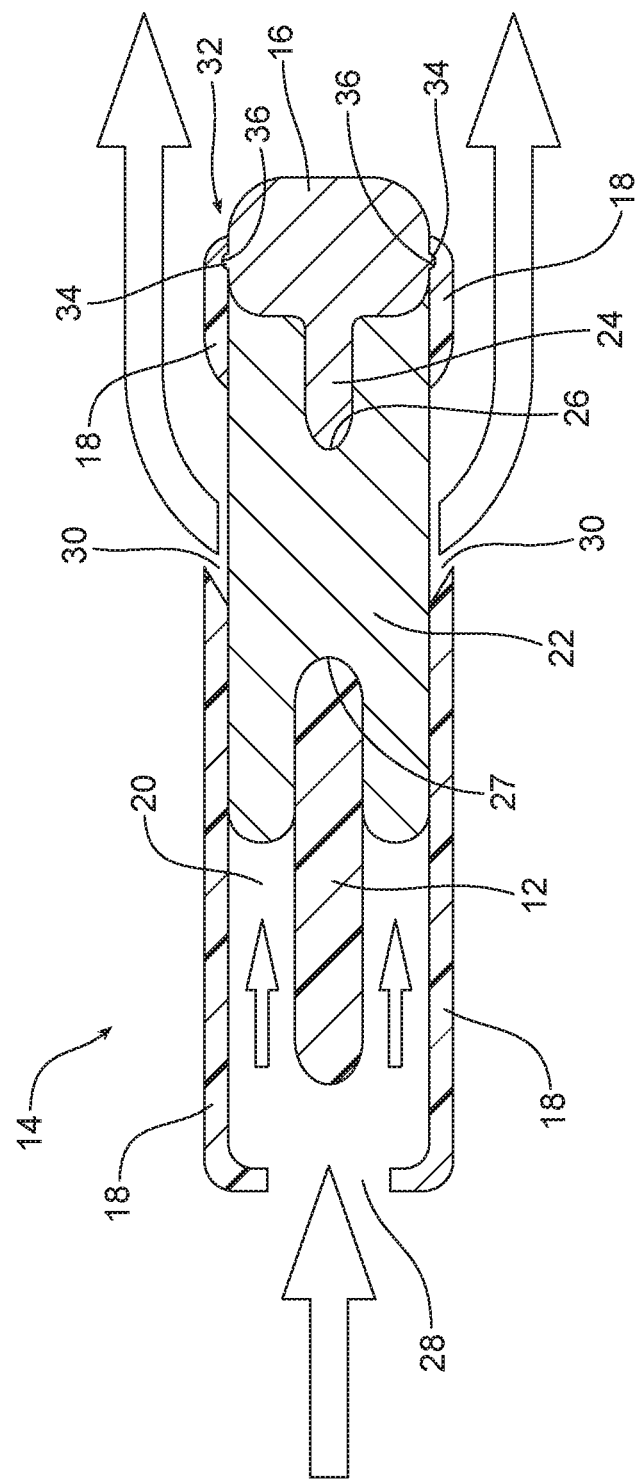
FIG. 2 is a detailed cross-sectional view through the actuator of the vent register illustrated in FIG. 1.
Figure 3:
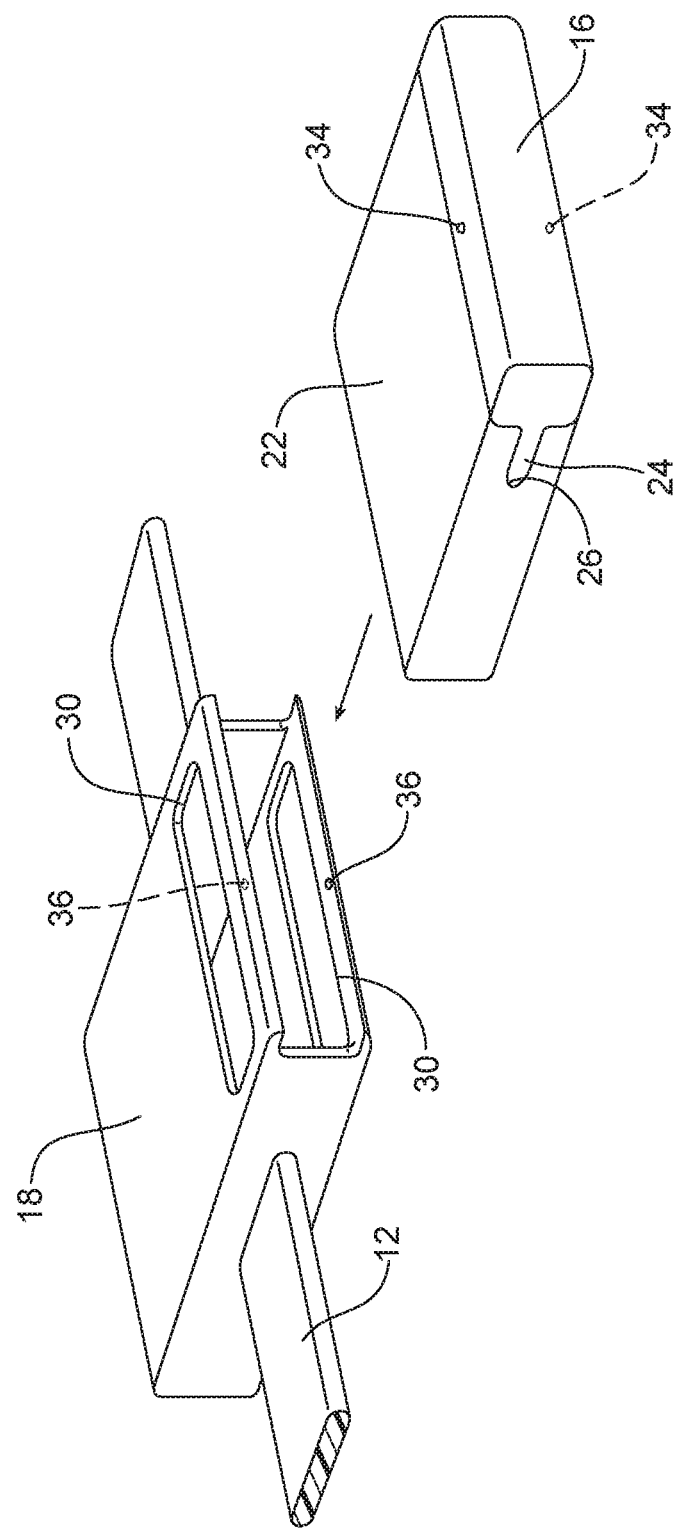
FIG. 3 is an exploded view of the actuator illustrated in FIG. 2.

As illustrated in FIGS. 1-3, the actuator 14 includes a first section 16, a second section 18 and a scent compartment 20 defined between the first section and the second section. In the illustrated embodiment, the second section 18 of the actuator 14 is integral with the adjustable vane 12 and, therefore, may be molded from a polymer or composite material as a single component structure.

A fragrance element 22 is carried on the actuator 14. In the illustrated embodiment the fragrance element 22 comprises a strip of porous material holding a volatile fragrance that is released into an airstream (note action arrows in FIG. 2) that travels across, over and/or through the strip.

The first section 16 of the actuator 14 includes a receiver 24 for holding the fragrance element 22. As best illustrated in FIGS. 2-4, the receiver 24 may comprise a lug that engages in a matching bore 26 of the fragrance element or strip 22. The fragrance element 22 includes an opening 27 for receiving the vane 12 when fully seated in the scent compartment 20.

As best illustrated in FIGS. 2-3, the second section 18 of the actuator 14 that is fixed to the adjustable vane 12 includes an air inlet 28 that is in communication with the scent compartment 20 and, therefore, the fragrance element 22 held therein. The second section 18 of the actuator 14 also includes an air outlet 30 also in communication with the scent compartment 20 and the fragrance element 22 held therein. More specifically, in the illustrated embodiment, the air outlet 30 comprises two openings: one opening in each of the upper and lower surfaces of the first section 16.

When one wishes to insert or change the fragrance element 22 in the scent compartment 20 of the actuator 14, one grips the first section 16 and pulls outwardly away from the second section 18 with a sufficient force to overcome the resilient latch 32 that secures the two sections together. In the illustrated embodiment, that resilient latch comprises two opposed ribs 34 on the first section 16 and two cooperating notches 36 in the second section 18 that receive and hold the ribs when the two sections are fully seated and engaged together. Here, it should be appreciated that the resilient latch 32 may assume any other form or construction appropriate for the intended purpose.

Once the first section 16 of the actuator 14 has been removed from engagement with the second section 18, it is a simple matter to grasp the fragrance element 22 and pull it from the lug 24. A new fragrance element 22 may then be inserted onto the lug 24. That new fragrance element 22 may be the same fragrance as the fragrance element that was removed from the lug 24 or a new or different scent as desired by the user.

After inserting the new fragrance element 22 onto the lug 24 of the first section 16, the first section 16 is aligned with the second section 18 and the two sections are reconnected. Once the first section 16 is fully seated in the second section 18, the resilient latch 32 again engages to secure the two sections together with the fragrance element 22 held on the lug 24 and captured within the scent compartment 20.

Whenever an airstream is forced through the ventilation duct to the vent register 10, a portion of that airstream will pass through the air inlet 28 in the second section 18 of the actuator 14, pass through the scent compartment 20, over across and through the fragrance element 22 so that some of the volatile fragrance or scent held on that element is entrained in the airstream, and then pass through the air outlet 30. Thus, it should be appreciated that the entrained scent is then distributed into the conditioned area or passenger compartment of the motor vehicle, freshening the air and improving the air quality to the satisfaction of the vehicle operator.

Consistent with the above description, a method is also provided of distributing a fragrance in a passenger compartment of a motor vehicle. That method may be broadly described as including the step of directing an airflow from a ventilation duct through a scent compartment 20 in an adjustment vane actuator 14 of a vent register 10 (see action arrows of FIG. 2). Further, the method may include positioning a fragrance element 22 in the scent compartment 20 such as in the manner described above.

The foregoing has been presented for purposes of illustration and description. It is not intended to be exhaustive or to limit the embodiments to the precise form disclosed. Obvious modifications and variations are possible in light of the above teachings. For example, the fragrance element 22 may be permanently attached to the lug 24 of the first section 16. In such an embodiment, when one changes the fragrance element, the first section 16 is also changed. All such modifications and variations are within the scope of the appended claims when interpreted in accordance with the breadth to which they are fairly, legally and equitably entitled.

What is claimed:
1. A vent register, comprising:
an adjustable vane;
a fragrance element;
an actuator; and
a resilient latch wherein (a) said actuator is carried on said adjustable vane and includes a first section, a second section and a scent compartment defined between said first section and said second section, (b) said first section includes a receiver holding said fragrance element, (c) said second section is fixed to said adjustable vane and includes an air inlet and an air outlet in communication with said scent compartment, (d) said fragrance element includes an opening adapted to receive said adjustable vane when fully seated in the scent compartment and (e) said resilient latch secures said first section with said second section.

2. The vent register of claim 1, wherein said fragrance element is a fragrance strip and said receiver includes a lug that engages said fragrance strip.

3. The vent register of claim 2, wherein said second section is integral with said adjustable vane so as to be a single component structure.

* * * * *